United States Patent
Vivilecchia et al.

(10) Patent No.: US 6,509,350 B2
(45) Date of Patent: Jan. 21, 2003

(54) STABILIZED PHARMACEUTICAL COMPOSITIONS COMPRISING ACID DONORS

(75) Inventors: Richard V. Vivilecchia, Rockaway, NJ (US); Bruce A. Ross, Fredon, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/931,750

(22) Filed: Aug. 17, 2001

(65) Prior Publication Data

US 2002/0013338 A1 Jan. 31, 2002

Related U.S. Application Data

(60) Division of application No. 08/472,412, filed on Jun. 6, 1995, now Pat. No. 6,300,362, which is a continuation of application No. 08/068,003, filed on May 27, 1993, now abandoned, which is a continuation of application No. 07/730,320, filed on Jul. 15, 1991, now abandoned, which is a continuation-in-part of application No. 07/557,234, filed on Jul. 25, 1990, now abandoned.

(51) Int. Cl.⁷ .............................................. A61K 31/47
(52) U.S. Cl. ...................... 514/307; 546/146; 562/575
(58) Field of Search ........................ 514/307; 546/146; 562/575

(56) References Cited

U.S. PATENT DOCUMENTS

| | | | |
|---|---|---|---|
| 4,344,949 A | | 8/1982 | Hoefle et al. |
| 4,470,972 A | | 9/1984 | Gold et al. |
| 4,500,713 A | * | 2/1985 | Suh et al. |
| 4,743,450 A | | 5/1988 | Harris et al. |
| 4,793,998 A | | 12/1988 | Murthy et al. |
| 4,808,413 A | | 2/1989 | Joshi et al. |
| 4,808,608 A | | 2/1989 | Guindon et al. ............. 514/411 |
| 4,830,853 A | * | 5/1989 | Murthy et al. |
| 4,912,096 A | | 3/1990 | Sudilovsky |
| 4,940,719 A | | 7/1990 | Gillard et al. ............... 514/318 |
| 4,952,566 A | | 8/1990 | Sakamaki et al. |
| 5,158,777 A | | 10/1992 | Abramowitz et al. |

FOREIGN PATENT DOCUMENTS

| | | |
|---|---|---|
| EP | 12401 | 6/1980 |
| EP | 264887 | 4/1988 |
| EP | 264888 | 4/1988 |
| GB | 895027 | 4/1962 |
| GB | 1317234 | 5/1973 |
| GB | 1437788 | 6/1976 |
| GB | 2101484 | 1/1983 |
| ZA | 87/06048 | 4/1988 |
| ZA | 88/08734 | 7/1989 |

OTHER PUBLICATIONS

Merck Index Disclosure 4682, 1983.
Physical Pharmacy, p. 389 (1983).
Pharmaceutical Research, vol. 4, No. 5, pp. 392–397 (1987).
J.Med.Chem., vol. 32, pp. 1600–1606 (1989).

* cited by examiner

Primary Examiner—Shailendra Kumar
(74) Attorney, Agent, or Firm—Joseph J. Borovian

(57) ABSTRACT

The invention relates to the use of certain acid donors as stabilizers in pharmaceutical compositions, and to the stabilized pharmaceutical compositions resulting therefrom.

28 Claims, No Drawings

STABILIZED PHARMACEUTICAL COMPOSITIONS COMPRISING ACID DONORS

This is a divisional of application Ser. No. 08/472,412, filed Jun. 6, 1995, now issued as U.S. Pat. No. 6,300,362, which is a continuation of application Ser. No. 08/068,003, filed May 27, 1993, which is a continuation of application Ser. No. 07/730,320, filed Jul. 15, 1991, which is a continuation-in-part of application Ser. No. 07/557,234, filed Jul. 25, 1990, the latter three of which are now abandoned.

BACKGROUND OF THE INVENTION

The present invention relates to the use of certain acid donors as stabilizers in pharmaceutical compositions, and to the stabilized pharmaceutical compositions resulting therefrom.

There are a number of pharmaceutical compositions which suffer from instability problems due to the fact that the active component is susceptible to certain types of degradation, thereby diminishing their attractiveness and, in some cases, rendering them unsuitable from a commercial standpoint. For example, several ACE (Angiotensin Converting Enzyme) inhibitor-containing compositions suffer from this drawback since certain ACE inhibitors degrade readily in pharmaceutical dosage forms. More particularly, and as is the case with other ACE inhibitors such as Quinapril and Enalapril, Spirapril degrades readily in dosage forms to the diketo piperazine (the internal cyclization product) and the diacid (the ester hydrolysis product). Accordingly, in view of their usefulness in treating hypertension, a number of research endeavors have been directed to overcoming the instability problem associated with ACE inhibitor-containing compositions, without appreciable success.

DESCRIPTION OF THE PRIOR ART

European Patent Application 264,888 is directed to the stabilization of ACE inhibitor-containing pharmaceutical compositions employing ascorbic acid alone or a combination of ascorbic acid with fumaric acid, maleic acid and/or citric acid as the stabilizing component(s).

U.S. Pat. No. 4,743,450 is also directed to the stabilization of ACE inhibitor-containing pharmaceutical compositions employing, as the stabilizer component, a combination of an alkali or alkaline earth metal salt (preferably, magnesium carbonate) and a saccharide (preferably, mannitol or lactose).

Although each of the above patents represents an attempt to overcome the instability problems associated with ACE inhibitor-containing compositions, there still exists a dire need for ACE inhibitor-containing compositions exhibiting improved stability, especially in the presence of moisture. To this end, the present invention is directed to pharmaceutical compositions, particularly ACE inhibitor-containing compositions, exhibiting improved stability.

OBJECTS OF THE INVENTION

It is, therefore, an object of the present invention to provide new stabilized pharmaceutical compositions.

It is another object of the present invention to provide new stabilized pharmaceutical compositions comprising a select group of acid donors as the stabilizing component thereof.

It is still another object of the present invention to provide new stabilized ACE inhibitor-containing pharmaceutical compositions.

It is yet still another object of the present invention to provide new stabilized ACE inhibitor-containing pharmaceutical compositions comprising a select group of acid donors as the stabilizing component thereof.

ADVANTAGES OF THE INVENTION

The stabilized pharmaceutical compositions of the instant invention exhibit a number of advantages as follows:

1) The active component, e.g., an ACE inhibitor, is virtually preserved from any type of degradation.
2) They exhibit an extended shelf-life under normal storage conditions.
3) They are insensitive to moisture and, in fact, the stability improves with an increase in moisture.
4) They exhibit minimal, if any, discoloration over a significant period of time.
5) They exhibit minimal, if any, instability when employed in the presence of colorants.

DESCRIPTION OF THE INVENTION

The attainment of the above objects and advantages is made possible by the use of certain acid donors and, more particularly, a select group of hydrochloric acid donors. In comparison to certain acidifiers which have previously been employed as stabilizers in pharmaceutical compositions, e.g., citric acid, maleic acid, ascorbic acid, etc., the acid donors of the present invention release the more volatile hydrochloric acid and, therefore, effect a greater diffusion through the dosage form matrix. Although any compounds which produce hydrochloric acid would be suitable in the practice of the instant invention, preferred acid donors include amino acid hydrochlorides and Lewis acid chlorides. The preferred amino acid hydrochlorides are glycine hydrochloride, glutamic acid hydrochloride, betaine hydrochloride, alanine hydrochloride, valine hydrochloride, lysine hydrochloride, arginine hydrochloride and aspartic acid hydrochloride, whereas the preferred Lewis acid chlorides are ferric chloride, zinc chloride and aluminum chloride. The more preferred amino acid hydrochlorides are glycine hydrochloride, glutamic acid hydrochloride and betaine hydrochloride, whereas the more preferred Lewis acid chloride is ferric chloride. The most preferred acid donor is glycine hydrochloride.

Although, in general, the hydrochloric acid donor can be employed in any amount which will prevent degradation of the active component, e.g., an ACE inhibitor, the amount of the hydrochloric acid donor employed is between 1% and 25%, preferably between 1% and 20%, more preferably between 1% and 15%, most preferably between 1 and 10%, based on the total weight of the pharmaceutical composition.

Although the essence of the instant invention, viz., the use of a select group of hydrochloric acid donors as stabilizers in pharmaceutical compositions, would apply to all pharmaceutical compositions where buffering to a low pH for required stability is essential, it has particularly been found useful when applied to ACE inhibitor-containing pharmaceutical compositions since, as indicated above, many ACE inhibitors degrade readily in pharmaceutical dosage forms. In general, all ACE inhibitor-containing pharmaceutical compositions wherein the ACE inhibitor employed is prone to form diketopiperazine degradation products would benefit from the use of a select group of hydrochloric acid donors as stabilizers therefor. For example, one class of ACE inhibitors to which the instant invention would apply are compounds of formula I:

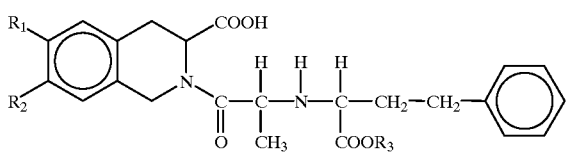

wherein $R_1$ and $R_2$, independently, are hydrogen or a group $-OC_nH_{2n+1}$, where n is 1 to 5; and $R_3$ is hydrogen or a group $-C_nH_{2n+1}$, where n is as defined above.

In the above formula, preferred compounds are those where $R_1$ and $R_2$ have the same significance. More preferred compounds of the above formula are those where $R_1$ and $R_2$ are both hydrogen or methoxy and $R_3$ is hydrogen or methyl. The most preferred compound of the above formula is Quinapril having the formula

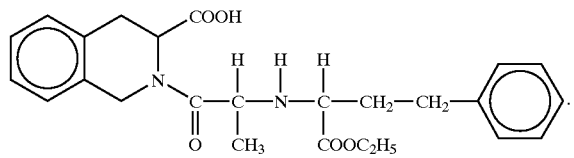

All of the above compounds are known, having been previously described in U.S. Pat. No. 4,344,949. Moreover, their usefulness in treating hypertension as well as methods for their preparation are set forth therein.

Another class of ACE inhibitors to which the invention would apply are compounds of formula II:

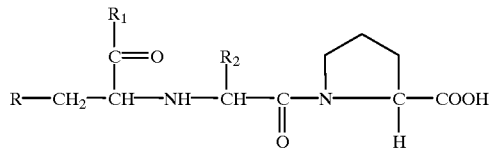

wherein R is $C_1$–$C_6$ alkyl, benzyl, benzylthio, benzyloxy, phenylthio or phenoxy;

$R_1$ is hydroxy or $C_1$–$C_6$ alkoxy;

and $R_2$ is hydrogen, $C_1$–$C_6$ alkyl or $C_1$–$C_6$ aminoalkyl.

In the above formula, preferred compounds are those wherein R is benzyl, $R_1$ is $C_1$–$C_6$ alkoxy and $R_2$ is hydrogen, methyl or aminobutyl. More preferred compounds of the above formula are those wherein R is benzyl, $R_1$ is $C_1$–$C_4$ alkoxy and $R_2$ is hydrogen or methyl. The even more preferred compounds of the above formula are those wherein R is benzyl, $R_1$ is ethoxy and $R_2$ is methyl. The most preferred compound of the above formula is Enalapril having the formula

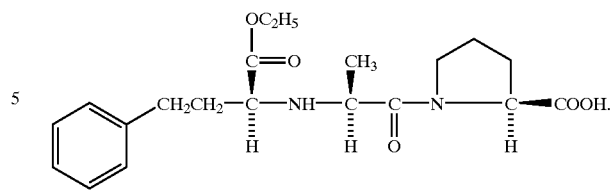

All of the above compounds of formula II are known, having been previously described in European Patent 12,401. Moreover, their usefulness in treating hypertension as well as methods for their preparation are set forth therein.

A particularly preferred class of ACE inhibitors to which the instant invention would apply are compounds of formula III:

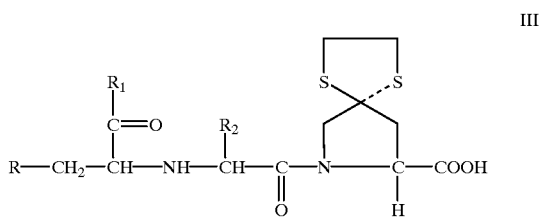

wherein R, $R_1$ and $R_2$ have the significances indicated above regarding the compounds of formula II.

The preferred, more preferred and even more preferred compounds of the above formula are as set forth above regarding the compounds of formula II. The most preferred compound of the above formula is Spirapril having the formula

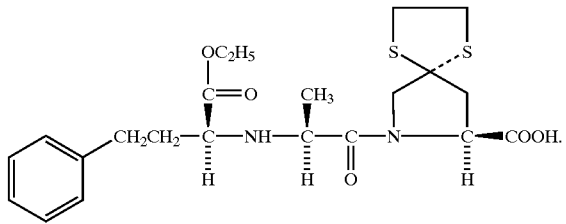

It should be noted that all of the compounds of formulae I, II and III form salts with various inorganic and organic acids and bases, which salts may be prepared by conventional methods. Therefore, it should be understood that all of such salts would also benefit from the use of the select group of hydrochloric acid donors as stabilizers thereof in accordance with the instant invention. Preferred are the pharmaceutically acceptable salts, i.e., the salts formed with pharmaceutically acceptable inorganic and organic acids and bases.

It should be noted that all of the compounds of formulae I, II and III form salts with various inorganic and organic acids and bases, which salts may be prepared by conventional methods. Therefore, it should be understood that all of such salts would also benefit from the use of the select group of hydrochloric acid donors as stabilizers therefor in accordance with the instant invention.

The amount of the active component, e.g., an ACE inhibitor, in the stabilized pharmaceutical compositions of the instant invention is between 0.5% and 50%, preferably between 0.75% and 25%, more preferably between 0.75% and 20%, most preferably between 0.75% and 15%, based on the total weight of the pharmaceutical composition.

The weight ratio of the active component, e.g., ACE inhibitor, to the hydrochloric acid donor may be determined in conventional manner. The preferred weight ratio of the active component to the hydrochloric acid donor is 2.5:1 to 1:7, more preferably 2:1 to 1:2.

As indicated above, all of the compounds of formulae I, II and III are known and their usefulness in treating hypertension is also well known. Accordingly, the daily dosages at which said compounds are employed as well as typical unit dosages of said compounds are well documented in the literature.

Although the stabilized ACE inhibitor-containing compositions may be in any form, the solid forms are preferred, more preferably tablets, capsules and caplets.

In addition to the active component, e.g., an ACE inhibitor, and the stabilizing component, e.g., glycine hydrochloride, the stabilized compositions of the instant invention will typically contain a pharmaceutically acceptable carrier. Generally, they are compounds which do not contain groups which would significantly interfere with either the active component or the stabilizing component. For example, sugars such as lactose, sucrose, mannitol and sorbitol are quite suitable; as are starches such as corn starch and tapioca starch; cellulose and derivatives thereof such as sodium carboxymethyl cellulose, ethyl cellulose and methyl cellulose; calcium phosphates such as dicalcium phosphate; sodium sulfate; and polyvinyl alcohol. Such type compounds are generally present in amounts of between 5% and 90%, preferably between 10% and 80%, based on the total weight of the pharmaceutical composition.

The stabilized compositions of the instant invention may also contain optional ingredients that are normally employed in pharmaceutical formulations, the only qualification being that they must be compatible with the select group of hydrochloric acid donors so as not to interfere with their stabilizing function. Typical optional ingredients include lubricants, e.g., talc, alkaline earth metal stearates such as magnesium stearate and calcium stearate, and hydrogenated vegetable oils such as hydrogenated cottonseed oil; binders such as polyvinylpyrrolidone and gelatin; and disintegrants such as microcrystalline cellulose, cross-linked polyvinyl-pyrrolidone and alginic acid. Other optional ingredients are fillers, water scavengers, buffers, preservatives, antioxidants, colorants and flavoring agents. The total amount of the optional ingredients in the stabilized compositions of the instant invention is not critical. In general, the total amount of the optional ingredients is consistent with the amount of the active component, stabilizer and pharmaceutically acceptable carrier, i.e., the total amount will be equivalent to the remainder of the pharmaceutical compositions.

The stabilized compositions of the instant invention can be prepared by any of the conventionally employed processing techniques such as the wet granulation process. The technique is preferably chosen to ensure a homogeneous distribution of the active component and a homogeneous distribution of the hydrochloric acid donor over or among the active component particles. Conveniently, the hydrochloric acid donor is distributed in a liquid form, e.g. an aqueous solution used as a granulating liquid.

Other active components that are contemplated include those with a —NH—CH—CO—N—C—COOH moiety as in the above formulae I, II and III, e.g., the diacid form of Spirapril, viz., Spiraprilate. Such compounds include Ramipril, Perindopril, Indolapril, Lisinopril, Alacepril, Trandolapril, Benazapril, Libenzapril, Delapril and Cilazapril.

The following examples are for the purpose of illustration only and are not intended in any way to limit the scope of the instant invention.

EXAMPLE 1

Below are stabilized compositions in accordance with the instant invention in white tablet form:

| Ingredient | Amount (mg) A | B |
| --- | --- | --- |
| Quinapril hydrochloride | 40.0 | — |
| Enalapril hydrochloride | — | 40.0 |
| glycine hydrochloride | 40.0 | 40.0 |
| lactose | 277.5 | 277.5 |
| corn starch | 25.0 | 25.0 |
| talc | 15.0 | 15.0 |
| magnesium stearate | 2.5 | 2.5 |
| total | 400.0 | 400.0 |

EXAMPLE 2

The following compositions A–D represent stabilized compositions in accordance with the instant invention in white tablet form whereas composition E does not contain a stabilizer of the instant invention:

| Ingredient | Amount (mg) | | | | |
| --- | --- | --- | --- | --- | --- |
| | A | B | C | D | E |
| Spirapril hydrochloride | 3.06 | 3.06 | 3.06 | 3.06 | 3.19 |
| lactose, NF | 99.94 | 94.74 | 99.94 | 94.74 | 80.21 |
| starch, NF | 19.50 | 19.50 | 19.50 | 19.50 | 12.00 |
| povidone, USP | 2.60 | 2.60 | 2.60 | 2.60 | 2.00 |
| glycine hydrochloride | — | — | 2.60 | 2.60 | — |
| glutamic acid hydrochloride | 2.60 | 2.60 | — | — | — |
| silica gel, NF | — | 5.20 | — | 5.20 | 1.90 |
| colloidal SiO$_2$, NF | 1.30 | 1.30 | 1.30 | 1.30 | 0.10 |
| magnesium stearate, NF | 1.00 | 1.00 | 1.00 | 1.00 | 0.60 |
| total | 130.00 | 130.00 | 130.00 | 130.00 | 100.00 |

EXAMPLE 3

To demonstrate the effectiveness of the stabilizers of the instant invention against added moisture, the following results were obtained when the compositions of Examples 2A–2D were stored for 3 months at 30° C. and 75% relative humidity:

| | *Assay % | Diketo | Diacid |
| --- | --- | --- | --- |
| Example 2A | 99.6 | 0.0 | 0.1 |
| Example 2B | 100.0 | 0.0 | 0.2 |
| Example 2C | 99.6 | 0.0 | 0.1 |
| Example 2D | 99.9 | 0.0 | 0.2 |

*percent of original Spirapril hydrochloride content

EXAMPLE 4

To demonstrate the effectiveness of the stabilizers of the instant invention against an increase in temperature, the following results were obtained when the compositions of Example 2A and 2C were stored at 50° C. for varying periods of time. For purposes of comparison, below are the results obtained when the composition of Example 2E was stored at 50° C. for three months.

|  | Period (months) | *Assay % | Diketo | Diacid |
|---|---|---|---|---|
| Example 2A | 1 | 99.0 | 0.2 | 0.1 |
|  | 2 | 100.8 | 0.6 | 0.3 |
|  | 3 | 99.1 | 0.9 | 0.3 |
| Example 2C | 1 | 100.3 | 0.1 | 0.2 |
|  | 2 | 101.3 | 0.8 | 0.2 |
|  | 3 | 98.4 | 1.0 | 0.3 |
| Example 2E | 3 | 91.2 | 7.3 | 0.4 |

*percent of original Spirapril hydrochloride content

EXAMPLE 5

The following compositions A, B and D represent stabilized compositions in accordance with the instant invention in colored tablet form whereas composition C contains maleic acid, an acidifier disclosed in the prior art:

|  | Amount (mg) | | | |
|---|---|---|---|---|
| Ingredient | A | B | C | D |
| Spirapril hydrochloride | 3.06 | 3.06 | 3.06 | 6.00 |
| lactose, NF | 96.94 | 96.94 | 96.94 | 99.77 |
| starch, NF | 19.50 | 19.50 | 19.50 | 22.50 |
| povidone, USP | 2.60 | 2.60 | 2.60 | 3.00 |
| alginic acid | — | — | — | 13.00 |
| glycine hydrochloride | 2.60 | — | — | 3.00 |
| glutamic acid hydrochloride | — | 2.60 | — | — |
| maleic acid | — | — | 2.60 | — |
| carmine | 3.00 | 3.00 | 3.00 | — |
| iron oxide, red | — | — | — | 0.03 |
| colloidol SiO$_2$, NF | 1.30 | 1.30 | 1.30 | 1.50 |
| magnesium stearate, NF | 1.00 | 1.00 | 1.00 | 1.20 |
| total | 130.00 | 130.00 | 130.00 | 150.00 |

EXAMPLE 6

To demonstrate the effectiveness of the stabilizers of the instant invention against an increase in temperature in the presence of colorants, the following results were obtained when the carmine colored compositions of Examples 5A and 5B were stored at 50° C. for three months.

|  | *Assay % | Diketo | Diacid |
|---|---|---|---|
| Example 5A | 96.3 | 2.7 | ** |
| Example 5B | 96.0 | 1.8 | ** |

*percent of original Spirapril hydrochloride content
**interference from dye

EXAMPLE 7

To demonstrate that volatile acids such as hydrochloric acid are more effective stabilizers than non-volatile acids such as maleic acid, the following results were obtained when the compositions of Examples 5A and 5C were stored at 50° C. for varying periods of time:

|  | Period (months) | *Assay % | Diketo | **Diacid |
|---|---|---|---|---|
| Example 5A | 1 | 98.4 | 1.1 | 1 |
|  | 2 | 105.2 | 3.1 | 2 |
|  | 3 | 96.3 | 2.7 | 2 |
| Example 5C | 1 | 91.6 | 5.1 | 1 |
|  | 2 | 89.2 | 14.8 | 2 |
|  | 3 | 84.6 | 10.0 | 2 |

*percent of original Spirapril hydrochloride content
**interference from dye

EXAMPLE 8

The following compositions A–D represent stabilized compositions in accordance with the instant invention in white tablet form whereas composition E does not contain a stabilizer of the instant invention:

|  | Amount (mg) | | | | |
|---|---|---|---|---|---|
| Ingredient | A | B | C | D | E |
| Spirapril hydrochloride | 3.3 | 3.3 | 3.3 | 3.3 | 3.3 |
| lactose, NF | 360.0 | 360.0 | 360.0 | 360.0 | 360.0 |
| glycine hydrochloride | 20.0 | — | — | — | — |
| ferric chloride | — | 20.0 | — | — | — |
| betaine hydrochloride | — | — | 20.0 | — | — |
| glutamic acid hydrochloride | — | — | — | 20.0 | — |
| colloidal SiO$_2$, NF | 1.0 | 1.0 | 1.0 | 1.0 | 1.0 |
| stearic acid, NF | 16.0 | 16.0 | 16.0 | 16.0 | 16.0 |
| total | 400.3 | 400.3 | 400.3 | 400.3 | 380.3 |

EXAMPLE 9

To demonstrate the effectiveness of the stabilizers of the instant invention against an increase in temperature and added moisture, the following results were obtained when the compositions of Examples 8A–8D were stored for 72 hours. For purposes of comparison, below are the results obtained when the composition of Example 8E was stored for 72 hours under the same conditions.

|  | Temp. (° C.) | % Water | *Assay % | Diketo | Diacid |
|---|---|---|---|---|---|
| Example 8A | 0 | 0 | 94 | 0.1 | 0.10 |
|  | 65 | 0 | 91 | 0.6 | 0.05 |
|  | 65 | 5 | — | — | — |
|  | 65 | 10 | 92 | 0.7 | 0.10 |
| Example 8B | 0 | 0 | 62 | 0.3 | 0.80 |
|  | 65 | 0 | 66 | 0.4 | 0.60 |
|  | 65 | 5 | 72 | 0.7 | 1.40 |
|  | 65 | 10 | 66 | 1.3 | 3.10 |
| Example 8C | 0 | 0 | 94 | 0.1 | 0.40 |
|  | 65 | 0 | 91 | 4.0 | 0.03 |
|  | 65 | 5 | 94 | 0.9 | 0.07 |
|  | 65 | 10 | 95 | 0.8 | 0.14 |
| Example 8D | 0 | 0 | 95 | 0.2 | 0.03 |
|  | 65 | 0 | 91 | 3.6 | 0.03 |
|  | 65 | 5 | 97 | 0.4 | 0.10 |
|  | 65 | 10 | 94 | 0.4 | 0.20 |
| Example 8E | 0 | 0 | 93 | 0.1 | 0.05 |
|  | 65 | 0 | 87 | 6.0 | 0.04 |
|  | 65 | 5 | 79 | 9.0 | 0.20 |
|  | 65 | 10 | 65 | 17.0 | 0.30 |

EXAMPLE 10

To demonstrate the extended shelf-life of a stabilized composition in accordance with the instant invention, the following results were obtained when the composition of Example 5A was stored for an extended period under various conditions:

| Period | 30° C. | | 40° C. | | 50° C. | | 30° C./75% RH | |
|---|---|---|---|---|---|---|---|---|
| (months) | DK | DA | DK | DA | DK | DA | DK | DA |
| 0 | 0.4 | 0.0 | — | — | — | — | — | — |
| 3 | 0.4 | 0.1 | 1.3 | 0.2 | 2.5 | 0.2 | 0.4 | 0.1 |
| 6 | 0.5 | 0.2 | 1.7 | 0.2 | 3.0 | 0.1 | 0.5 | 0.1 |
| 9 | 0.9 | 0.2 | — | — | — | — | — | — |
| 12 | 1.1 | 0.2 | 2.6 | 0.1 | — | — | — | — |
| 24 | 1.5 | 0.2 | — | — | — | — | — | — |

DK = diketopiperazine
DA = diacid

What is claimed is:
1. A method of stabilizing a pharmaceutical composition containing an ACE inhibitor of formula I:

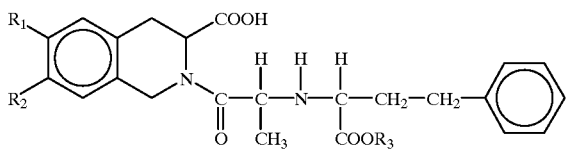

wherein $R_1$ and $R_2$, independently, are hydrogen or a group $-OC_nH_{2n+1}$, where n is 1 to 5; and $R_3$ is hydrogen or a group
$-C_nH_{2n+1}$, where n is as defined above; or a pharmaceutically acceptable salt thereof, comprising incorporating therein a stabilizing effective amount of a hydrochloric acid donor.

2. A stabilized pharmaceutical composition comprising an ACE inhibitor of formula I:

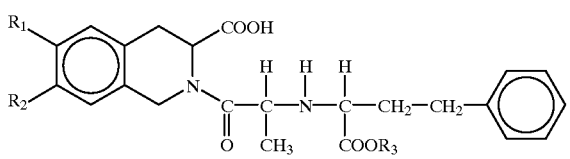

wherein $R_1$ and $R_2$, independently, are hydrogen or a group $-OC_nH_{2n+1}$, where n is 1 to 5;

and $R_3$ is hydrogen or a group $-C_nH_{2n+1}$; where n is as defined above;

or a pharmaceutically acceptable salt thereof and, as a stabilizer therefor, a hydrochloric acid donor.

3. A method according to claim 1 wherein the ACE inhibitor is a compound of formula I wherein $R_1$ and $R_2$ have the same significance, or a pharmaceutically acceptable salt thereof.

4. A method according to claim 3 wherein the ACE inhibitor is a compound of formula I wherein $R_1$ and $R_2$ are both hydrogen or methoxy and $R_3$ is hydrogen or ethyl, or a pharmaceutically acceptable salt thereof.

5. A method according to claim 4 wherein the ACE inhibitor is a compound having the formula

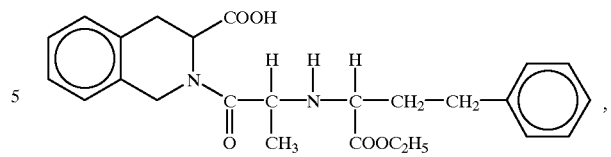

or a pharmaceutically acceptable salt thereof.

6. A method according to claim 1 wherein the hydrochloric acid donor is an amino acid hydrochloride or a Lewis acid chloride.

7. A method according to claim 6 wherein the amino acid hydrochloride is selected from the group consisting of glycine hydrochloride, glutamic acid hydrochloride, betaine hydrochloride, alanine hydrochloride, alanine hydrochloride, valine hydrochloride, lysine hydrochloride, arginine hydrochloride and aspartic acid hydrochloride.

8. A method according to claim 7 wherein the amino acid hydrochloride is selected from the group consisting of glycine hydrochloride, glutamic acid hydrochloride and betaine hydrochloride.

9. A method according to claim 8 wherein the amino acid hydrochloride is glycine hydrochloride.

10. A method according to claim 6 wherein the Lewis acid chloride is selected from the group consisting of ferric chloride, zinc chloride and aluminum chloride.

11. A method according to claim 10 wherein the Lewis acid chloride is ferric chloride.

12. A method according to claim 6 wherein the hydrochloric acid donor is present in an amount between 1% and 25%, based on the total weight of the composition.

13. A method according to claim 12 wherein the hydrochloric acid donor is present in an amount between 1% and 20%, based on the total weight of the composition.

14. A method according to claim 13 wherein the hydrochloric acid donor is present in an amount between 1% and 15%, based on the total weight of the composition.

15. A method according to claim 14 wherein the hydrochloric acid donor is present in an amount between 1% and 10%, based on the total weight of the composition.

16. A stabilized composition according to claim 2 wherein the ACE inhibitor is a compound of formula I wherein $R_1$ and $R_2$ have the same significance, or a pharmaceutically acceptable salt thereof.

17. A stabilized composition according to claim 16 wherein the ACE inhibitor is a compound of formula I wherein $R_1$ and $R_2$ are both hydrogen or methoxy and $R_3$ is hydrogen or ethyl, or a pharmaceutically acceptable salt thereof.

18. A stabilized composition according to claim 17 wherein the ACE inhibitor is a compound having the formula

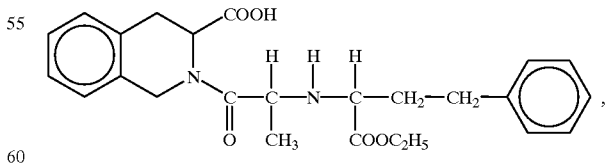

or a pharmaceutically acceptable salt thereof.

19. A stabilized composition according to claim 2 wherein the hydrochloric acid donor is an amino acid hydrochloride or a Lewis acid chloride.

20. A stabilized composition according to claim 19 wherein the amino acid hydrochloride is selected from the group consisting of glycine hydrochloride, glutamic acid hydrochloride, betaine hydrochloride, alanine hydrochloride, valine hydrochloride, lysine hydrochloride, arginine hydrochloride and aspartic acid hydrochloride.

21. A stabilized composition according to claim 20 wherein the amino acid hydrochloride is selected from the group consisting of glycine hydrochloride, glutamic acid hydrochloride and betaine hydrochloride.

22. A stabilized composition according to claim 21 wherein the amino acid hydrochloride is glycine hydrochloride.

23. A stabilized composition according to claim 19 wherein the Lewis acid chloride is selected from the group consisting of ferric chloride, zinc chloride and aluminum chloride.

24. A stabilized composition according to claim 23 wherein the Lewis acid chloride is ferric chloride.

25. A stabilized composition according to claim 19 wherein the hydrochloric acid donor is present in an amount between 1% and 25%, based on the total weight of the composition.

26. A stabilized composition according to claim 25 wherein the hydrochloric acid donor is present in a amount between 1% and 20%, based on the total weight of the composition.

27. A stabilized composition according to claim 26 wherein the hydrochloric acid donor is present in an amount between 1% and 15%, based on the total weight of the composition.

28. A stabilized composition according to claim 27 wherein the hydrochloric acid donor is present in an amount between 1% and 10%, based on the total weight of the composition.

* * * * *